United States Patent [19]

Hagiwara

[11] Patent Number: 5,646,725

[45] Date of Patent: Jul. 8, 1997

[54] FOREIGN MATTER INSPECTION APPARATUS FOR LARGE-SCALE SUBSTRATE

[75] Inventor: Tsuneyuki Hagiwara, Kawasaki, Japan

[73] Assignee: Nikon Corporation, Tokyo, Japan

[21] Appl. No.: 574,685

[22] Filed: Dec. 19, 1995

[30] Foreign Application Priority Data

Dec. 21, 1994 [JP] Japan ..................... 6-335534

[51] Int. Cl.⁶ ............................................. G01N 21/00
[52] U.S. Cl. ............................................ 356/237; 356/239
[58] Field of Search ........................... 356/237, 239, 356/429–431, 371, 445, 335–343; 250/562, 572, 571, 514

[56] References Cited

U.S. PATENT DOCUMENTS

| | | | |
|---|---|---|---|
| 4,643,569 | 2/1987 | Sullivan et al. | 356/237 |
| 4,898,471 | 2/1990 | Stonestrom et al. | 356/394 |
| 4,943,734 | 7/1990 | Johnson et al. | 250/572 |
| 5,043,589 | 8/1991 | Smedt et al. | 250/561 |
| 5,317,380 | 5/1994 | Allemand | 356/338 |

*Primary Examiner*—Frank Font
*Assistant Examiner*—Michael P. Stafira
*Attorney, Agent, or Firm*—Shapiro and Shapiro

[57] ABSTRACT

An apparatus for optically inspecting foreign matter attached to a surface of a substrate on which a pattern is formed, includes an optical scan device for forming an arcuated optical scan line by scanning illumination light on the surface of the substrate, a moving device for moving the substrate relative to the optical scan line in a predetermined direction, a light-receiving device for receiving scattered light from the foreign matter attached to the surface of the substrate, and outputting an electrical signal corresponding to the intensity of the scattered light, and a signal processing device for detecting the foreign matter on the basis of the electrical signal from the light-receiving device.

12 Claims, 15 Drawing Sheets

FOREIGN MATTER INSPECTION APPARATUS FOR LARGE-SCALE SUBSTRATE

BACKGROUND OF THE INVENTION

1. Field of the Invention

The present invention relates to a foreign matter inspection apparatus for a substrate and, more particularly, to an apparatus for detecting foreign matter attached to the surface of a substrate (e.g., a large-scale substrate such as a mask used in the manufacture of liquid crystal devices) on which patterns are formed.

2. Related Background Art

In a conventional foreign matter inspection apparatus, a light beam emitted by, e.g., a laser light source is deflected in a predetermined direction by a scanner such as a galvano mirror, a polygonal mirror, or the like, and is focused on the surface of a substrate via an f-θ lens or fsin⁻¹θ lens. With this operation, a linear scan line is formed across almost the total width of the substrate (almost the entire substrate in the scan direction) on the surface of the substrate to be inspected. Furthermore, the entire surface of the substrate is two-dimensionally scanned with the light beam by moving the scan line (light beam) relative to the substrate in a direction perpendicular to the scan line.

As described above, in the conventional foreign matter inspection apparatus, the linear scan line is formed on the surface of the substrate via the f-θ lens or fsin⁻¹θ lens. Therefore, when the size of a substrate to be inspected becomes large, the field angle required for the f-θ lens or fsin⁻¹θ lens increases. In order to obtain a large numerical aperture (NA) at such large field angle, the required lens diameter increases, resulting in high cost.

Also, as described above, the conventional foreign matter inspection apparatus uses the galvano mirror, polygonal mirror, or the like as a beam deflector required for forming the linear optical scan line. However, since the upper limit of the scan frequency of the galvano mirror is determined due to its reciprocal movement, the inspection speed is limited. On the other hand, it is difficult for the polygonal mirror to attain ideal optical performance since it is very difficult to attain plane tilt correction among planes.

SUMMARY OF THE INVENTION

The present invention has been made in consideration of the above situation, and has as its object to provide a foreign matter inspection apparatus for a large-scale substrate, which can inspect foreign matter attached to the surface of a large-scale substrate without using an f-θ lens or fsin⁻¹θ lens having a large lens diameter.

In order to achieve the above object, according to the present invention, there is provided a foreign matter inspection apparatus for optically inspecting foreign matter attached to a surface of a substrate on which a pattern is formed, comprising an optical scan device for forming an arcuated optical scan line by scanning illumination light on the surface of the substrate, a moving device for moving the substrate relative to the optical scan line in a predetermined direction, a light-receiving device for receiving scattered light from the foreign matter attached to the surface of the substrate, and outputting an electrical signal corresponding to an intensity of the scattered light, and a signal processing device for detecting the foreign matter on the basis of the electrical signal from the light-receiving device.

According to a preferred aspect of the present invention, the optical scan device comprises a reflection device having a reflection surface which is obliquely set with respect to the surface of the substrate, a driving device for rotating the reflection device about an axis perpendicular to the surface of the substrate, a focusing optical system for focusing the illumination light reflected by the reflection device onto the surface of the substrate in a spot pattern, and a control device for controlling the driving device to move the light focused in the spot pattern along the arcuated optical scan line upon rotation of the reflection device.

According to the present invention, the reflection device (rotary scanner), which has a reflection surface obliquely set with respect to the surface of a substrate, and is rotatable about an axis perpendicular to the surface of the substrate, is rotated, and light reflected by the reflection device is focused on the surface of the substrate to form an arcuated optical scan line. Therefore, no scan lens such as an f-θ lens for forming a linear optical scan line is required unlike in the prior art. As a result, using a lens which is not restricted in terms of its field angle, the design and manufacture of an optical system as an optical scan device are facilitated.

The foreign matter detection principle in a foreign matter inspection apparatus for a large-scale substrate according to the present invention will be described below.

The foreign matter inspection apparatus for a large-scale substrate of the present invention is designed not to erroneously detect a circuit pattern on a so-called large-scale substrate as foreign matter. Note that the large-scale substrate is a substrate (for example, a mask used in the manufacture of a liquid crystal display) used in the manufacture of, e.g., an F.P.D. (Flat Panel Display). In the case of such a substrate, dust having a size exceeding a diameter of about 0.8 μm need only be detected.

The beam spot size of a laser beam spot required for detecting foreign matter of such a size is about 50 μm. Within the beam spot having this size, no complicated periodic pattern such as a DRAM pattern is present. Therefore, it is only required not to erroneously detect light from the edge of an isolated pattern as light from foreign matter.

FIG. 14 and FIGS. 15A to 15C are views for explaining optical removal of pattern edge noise. Note that FIG. 14 shows the distributions of light beams on the spherical surface of a virtual sphere S. FIG. 15A shows the sphere S when viewed from the direction of a normal to an x-y plane, and FIGS. 15B and 15C are orthogonally projected views of the spherical surface shown in FIG. 14 onto the x-y plane.

Referring to FIG. 14, a circuit pattern P consisting of chromium is formed on the surface of a substrate 35 such as a glass reticle. Note that the surface of the substrate 35 agrees with the x-y plane. In FIG. 14, n indicates the direction of a normal to the surface of the substrate 35, which direction is perpendicular to the x- and y-axes.

In FIG. 14, a focused light beam I becomes obliquely incident on the chromium pattern P, and is scattered at a point D to generate light on a band D.B. including a point r on the spherical surface, where the incident light regularly reflected by the surface of the substrate 35 passes. The width, w (which is defined by the width, in the x-direction (or y-direction) in the x-y-plane, of the orthogonally projected area of the band D.B. onto the x-y plane, or is associated with a predetermined direction on the Fourier transformation plane of the pattern P), of the band D.B. depends on the solid angle, α, of the incident light beam, and at the point r, it agrees with the width (which is defined by the width, in the x-direction (or y-direction) in the x-y plane, of the orthogonally projected area of the bright spot of the point r onto the x-y plane, or is associated with a predetermined direction on the Fourier transformation plane of the pattern P) of the bright spot of the point r formed by reflected light when no pattern is formed.

FIG. 14 exemplifies a case wherein the pattern P has an edge in the x-direction. On the other hand, FIG. 15A shows a general example wherein the edge of a pattern P1 forms an angle β with the x-axis.

Referring to FIG. 15A, the band D.B.(β) of scattered light is generated to include the point r, and to extend in a direction perpendicular to the direction of the edge of the pattern P1. For this reason, the band D.B. (β) of the scattered light fluctuates about the point r through an angle of β=β' in accordance with the magnitude of β.

In FIGS. 14 and 15A, light-receiving surfaces A, B, and C (the light-receiving surfaces A, B, and C are assumed to be located on the sphere S) of three light-receiving elements are present within the region of backward scattering, and receive backward scattered light from foreign matter.

In FIG. 15A, if β' becomes smaller, reflected light with high directivity, i.e., scattered light D.B. (β), from the pattern P becomes incident on the light-receiving surface C, but no light becomes incident on the remaining light-receiving surfaces B and A. On the other hand, scattered light from foreign matter is almost uniformly generated within the region of backward scattering since it has no directivity. For this reason, the light-receiving surfaces A, B, and C receive scattered light components having almost equal light intensities.

In this manner, in order to avoid the pattern edge from being erroneously detected, a condition that the scattered light from the pattern P is not incident on all the light-receiving elements is necessary.

As described above, according to the present invention, scattered light generated from one point on the substrate is received by a plurality of light-receiving elements which receive light from different directions, and light from the pattern edge is removed by utilizing the directivity of scattered light. This technique will be explained below with reference to FIGS. 15B and 15C.

Referring to FIGS. 15B and 15C, regions obtained by orthogonally projecting the light-receiving surfaces onto the x-y plane are respectively represented by regions $A_1$, $B_1$, and $C_1$.

Note that the scattered light distribution formed by regions obtained by orthogonally projecting respective regions, where scattered light components from the incident point on the x-y plane of the incident light I pass, on the sphere S onto the x-y plane, roughly represents a Fourier transformation pattern with respect to the amplitude distribution of light waves incident on the pattern P1, and can be observed as a spatial frequency spectrum to have the zeroth-order light position, i.e., the orthogonally projected position r of reflected light as the center. Therefore, each of the regions $A_1$, $B_1$, and $C_1$ obtained by orthogonally projecting the light-receiving surfaces A, B, and C onto the x-y plane is a spatial frequency region representing the spatial frequency spectrum incident on the corresponding light-receiving surface.

In the following description, the Fourier transformation pattern as the orthogonally projected view of the above-mentioned distribution pattern of the scattered light is handled as the distribution pattern in a two-dimensional U-V orthogonal coordinate system to have the spectrum position r of regularly reflected light as an origin, and is expressed as the distribution on a U-V plane for the sake of simplicity.

Assume that the U-axis is parallel to the x-axis, and the V-axis is parallel to the y-axis.

How to set the spatial frequency regions of the light-receiving surfaces of the light-receiving elements will be described below with reference to FIGS. 15B and 15C.

FIGS. 15B and 15C are orthogonally projected views of the virtual sphere S onto the x-y plane. The width, in the x-direction, of a region $i_1$ (the spatial frequency region of the incident light I) obtained by orthogonally projecting a bright spot portion i, formed on a crossing portion between the incident light I and the spherical surface of the sphere S, onto the x-y plane is $i_w$ in FIG. 15B.

In the present invention, an optical scan line is formed by, e.g., a rotary scanner, and is formed in an arcuated pattern on the x-y plane (substrate surface) perpendicular to the plane of incidence. The respective light-receiving elements are disposed in a direction along the above-mentioned arcuated optical scan line.

Note that the plane of incidence is a y-n plane in FIG. 14, and an optical scan line c.l. is formed in an arcuated pattern on the x-y plane, as shown in FIGS. 14 and 15B. Therefore, the layout direction of the light-receiving elements extends substantially along the x-axis.

The size of the light-receiving surface of each light-receiving element is determined by the electrical S/N ratio that depends on the amount of the incident light I and the characteristics of a photoelectric conversion element, and the optical S/N ratio for optical stray light.

In FIG. 14, the light-receiving surfaces A, B, and C of the three light-receiving elements are ready to receive light with respect to an inspection point D. At this time, if the inner distance (a distance on the U-V plane) between the spatial frequency regions of the light-receiving surfaces A and C of the light-receiving elements is larger than the width of the spatial frequency region (a region obtained by orthogonally projecting the region, where the incident light passes, on the sphere S onto the x-y plane, or a region on the Fourier transformation plane where the incident light I regularly reflected by the substrate passes), in the U-direction, of the incident light I, light components reflected by the edge never become simultaneously incident on the three light-receiving surfaces A to C independently of the direction of the pattern edge.

Furthermore, if the inner distance (a distance on the U-V plane) between the spatial frequency regions of the light-receiving surfaces of the two outermost ones of light-receiving elements which are ready to receive light is larger than the width of the spatial frequency region, in the U-direction (x-direction on the U-V plane), of incident light independently of the number of light-receiving elements, light components reflected by the pattern edge never become simultaneously incident on all the light-receiving elements. This is because the width, in the U-direction on the U-V plane, of the spatial frequency region of scattered/diffracted light from the pattern edge becomes almost equal to the width, in the x-direction on the U-V plane, of the spatial frequency region of the incident light.

FIG. 15B shows a case wherein the interval, $x_1$, on the U-V plane, between the spatial frequency regions $A_1$ and $C_1$ of the light-receiving surfaces of the light-receiving elements is smaller than the width in the U-direction, of the region $i_1$ representing the spatial frequency region of the incident light, i.e., an example wherein the above-mentioned condition is not met. In this case, since the inner distance, $x_1$, on the U-V plane, between the spatial frequency regions $A_1$ and $C_1$ of the light-receiving surfaces is smaller than the width $i_w$, in the U-direction on the U-V plane, of the spatial frequency region of the incident light I, light components reflected by the pattern edges become simultaneously incident on the spatial frequency regions $A_1$ to $C_1$ of the three light-receiving surfaces. As a result, reflected light from the pattern edge cannot be distinguished from scattered light from foreign matter.

On the other hand, FIG. 15C shows a case wherein the interval $x_1$, on the U-V plane, between the spatial frequency regions $A_1$ and $C_1$ of the light-receiving surfaces of the light-receiving elements is larger than the width $i_w$, in the U-direction on the U-V plane, of the region $i_r$ representing the spatial frequency region of the incident light I, i.e., an example wherein the above-mentioned condition that reflected light from the pattern edge is not simultaneously incident on all the light-receiving elements is met. In this case, independently of the generation angle of band-shaped diffracted light having the bright spot position r of reflected light as the center, pattern scattered light does not become simultaneously incident on all the light-receiving surfaces A to C. As a result, reflected light from the pattern edge can be distinguished from scattered light from foreign matter on the basis of the intensities of scattered light components incident on the respective light-receiving elements. Note that the distribution pattern r is similar to the distribution pattern $i_1$ on the U-V plane, and their widths in the U-direction agree with each other.

The above and other objects, features and advantages of the present invention will be explained hereinafter and may be better understood by reference to the drawings and the descriptive matter which follows.

BRIEF DESCRIPTION OF THE DRAWINGS

FIGS. 15A to 15C are views for explaining the technique for optically removing pattern edge noise, in which FIG. 15A is a view showing the sphere S shown in FIG. 14 when viewed from the direction of a normal to an x-y plane, and FIGS. 15B and 15C are orthogonally projected views of the sphere shown in FIG. 14 onto the x-y plane.

DETAILED DESCRIPTION OF THE PREFERRED EMBODIMENTS

The preferred embodiments of the present invention will be described hereinafter with reference to the accompanying drawings.

Figure 1:
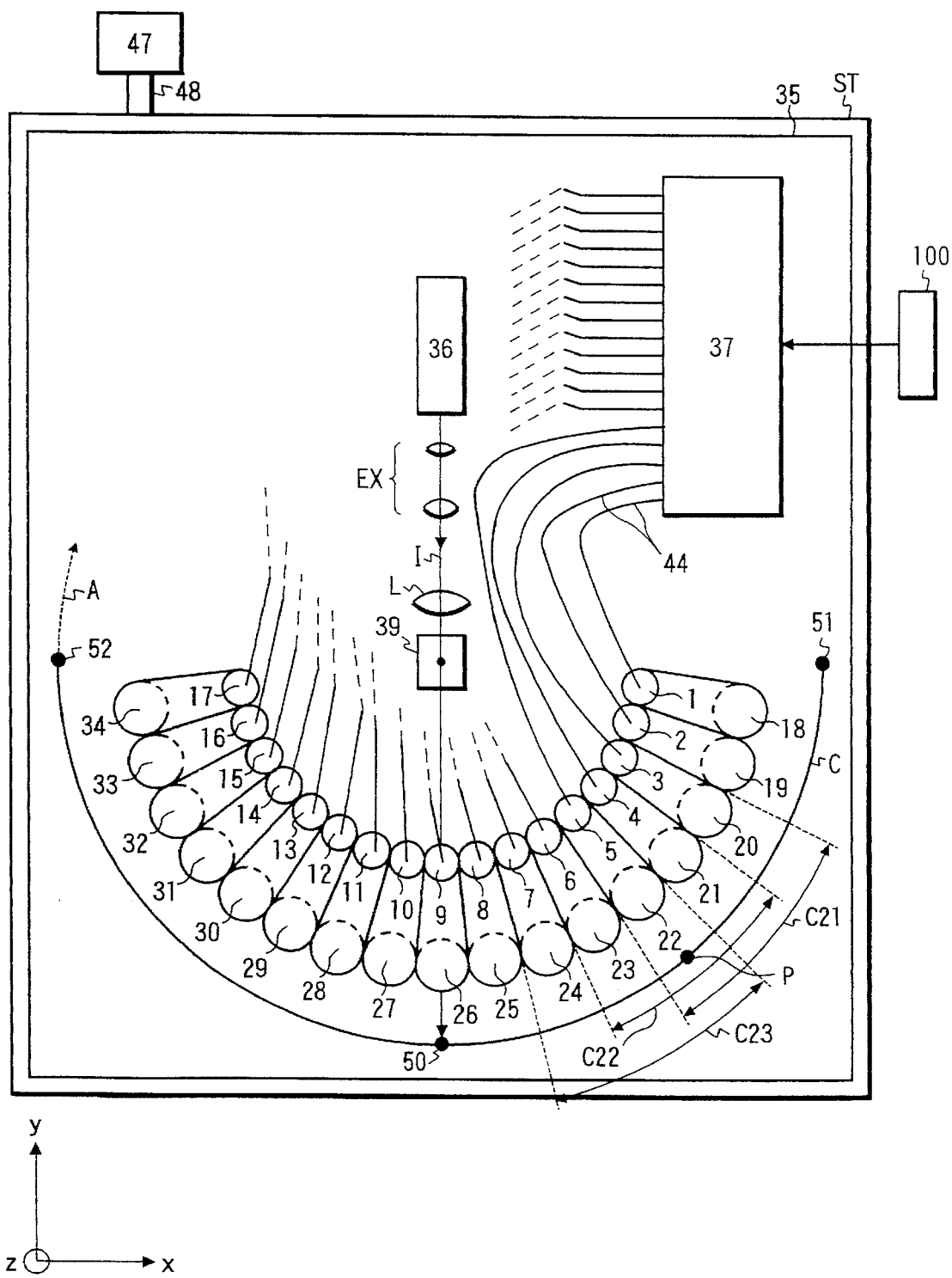
FIG. 1 is a schematic x-y plan view showing the arrangement of a foreign matter inspection apparatus according to the first embodiment of the present invention.
Figure 2:
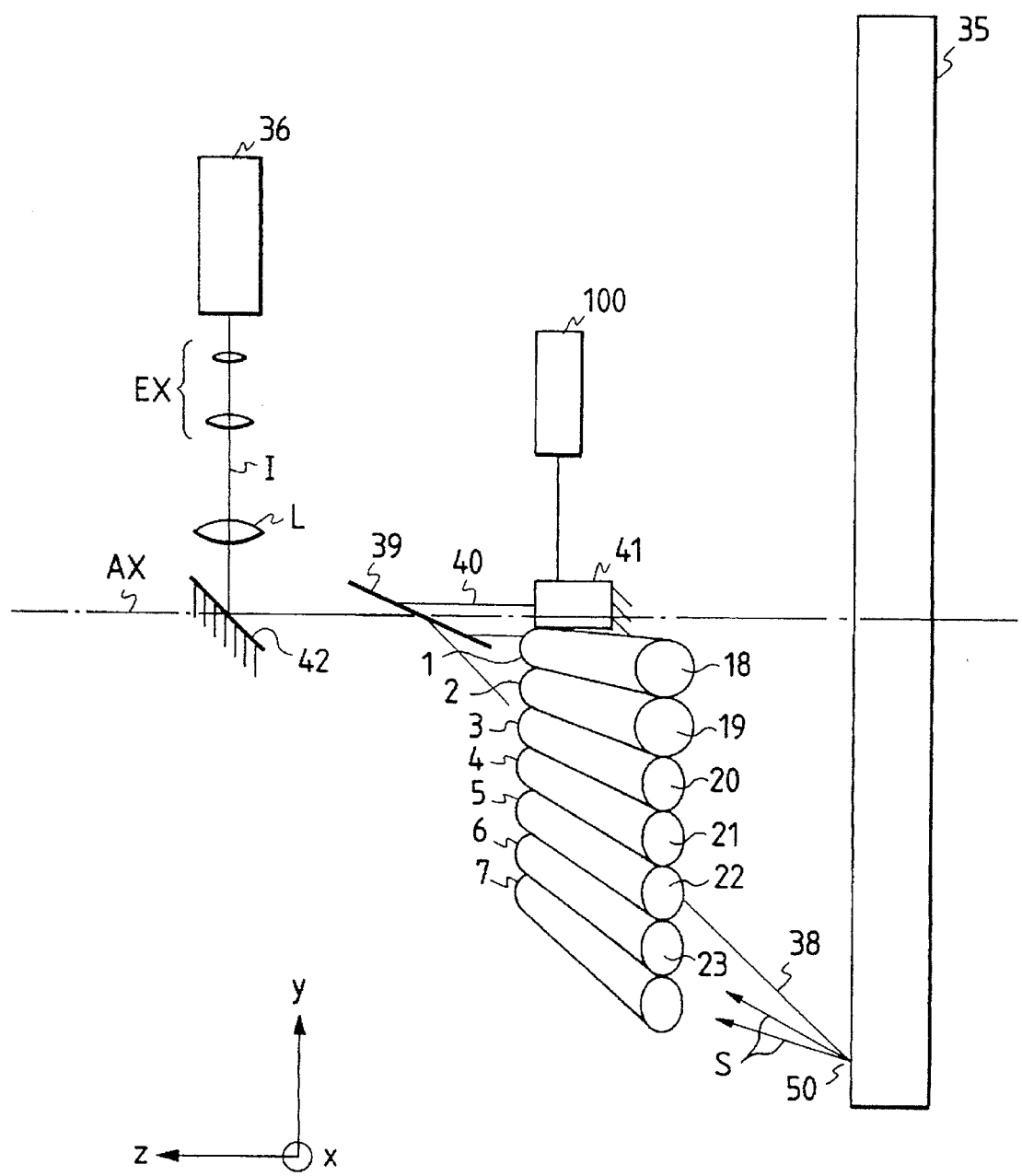
FIG. 2 is a schematic y-z plan view showing the arrangement of the foreign matter inspection apparatus according to the first embodiment of the present invention.
Figure 3:
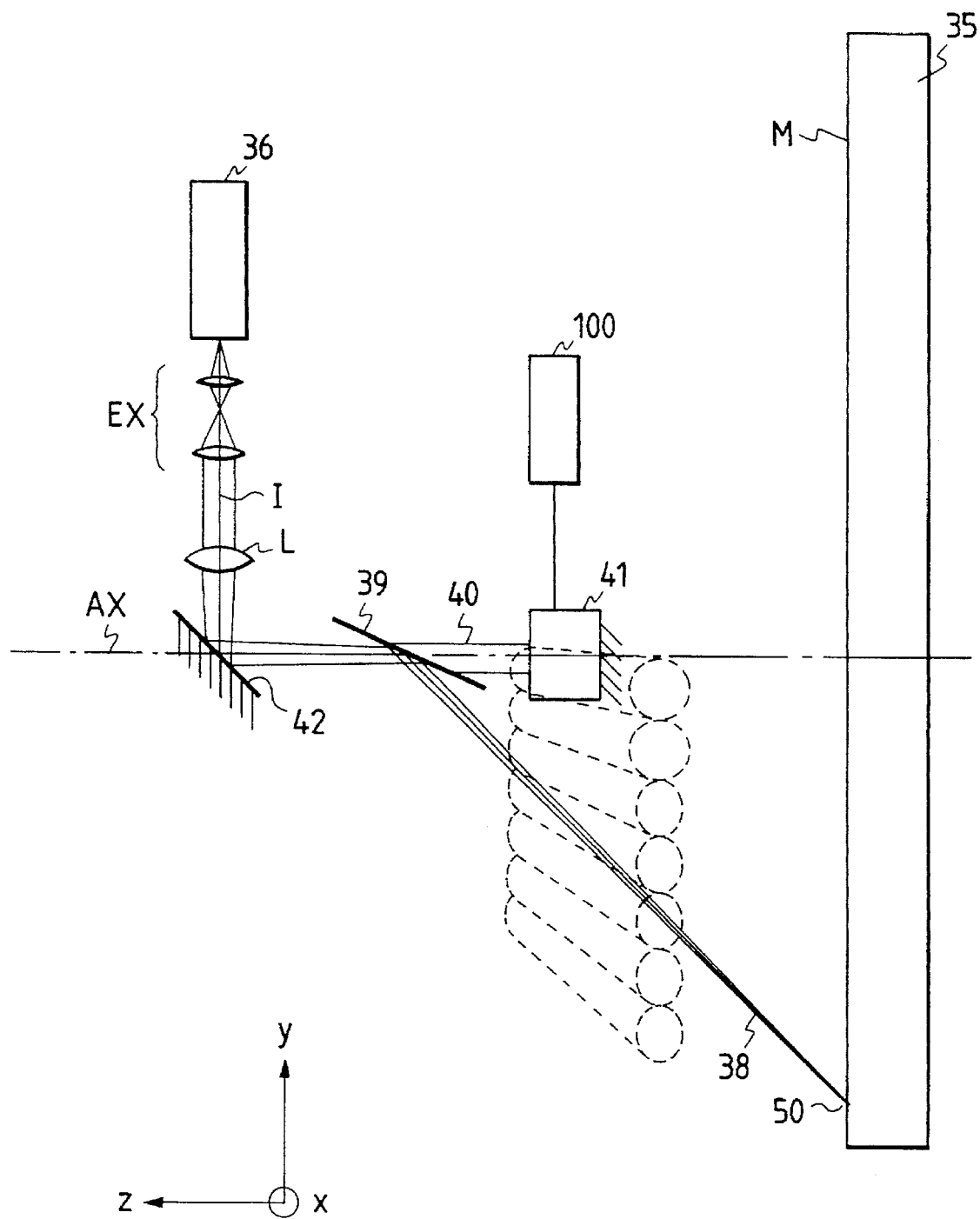
FIG. 3 is a schematic y-z plan view showing the arrangement of the foreign matter inspection apparatus according to the first embodiment of the present invention.
Figure 4:
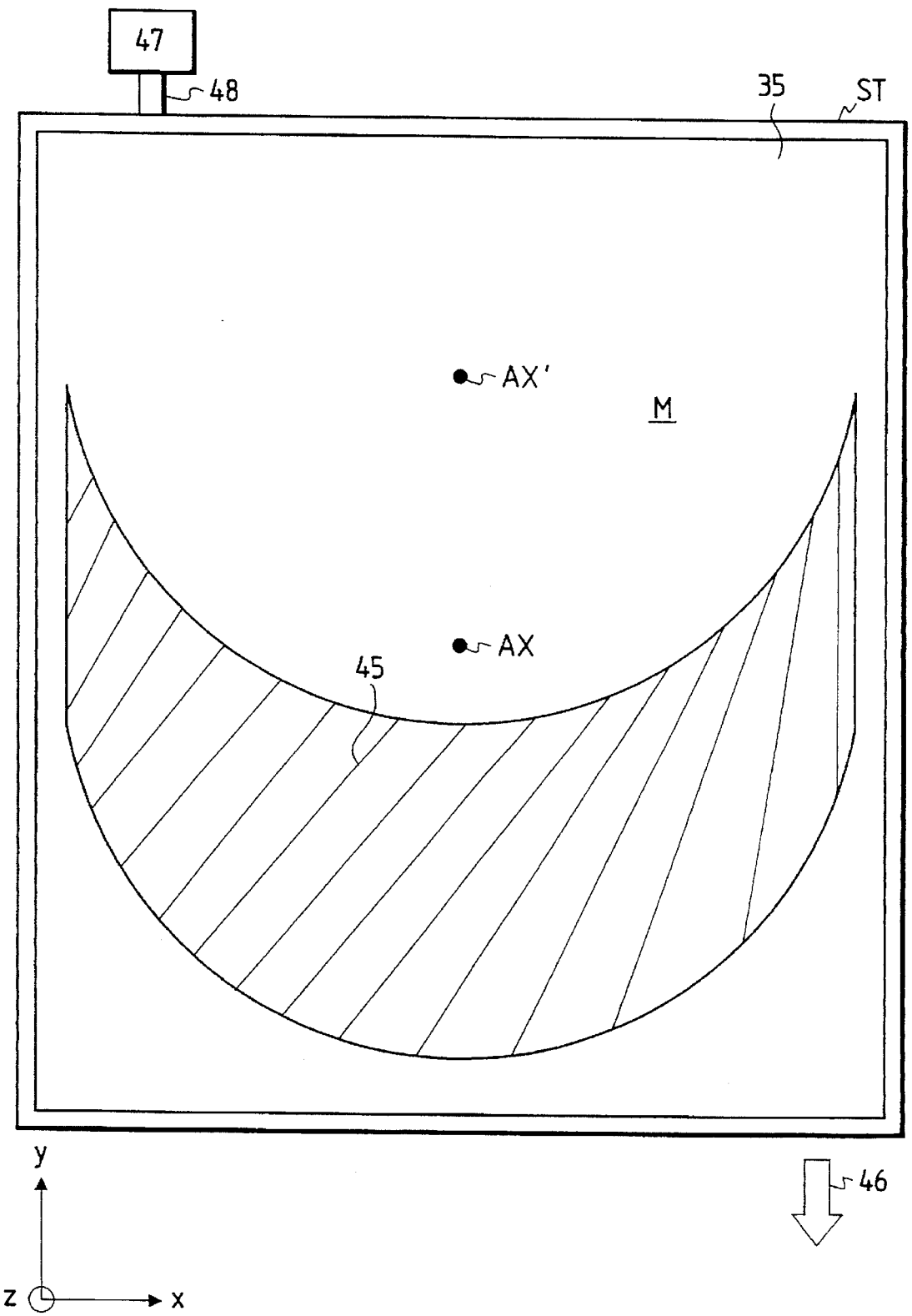
FIG. 4 is a schematic x-y plan view showing the arrangement of the foreign matter inspection apparatus according to the first embodiment of the present invention, and showing the execution process of foreign matter inspection.

FIG. 1 is a schematic view showing the arrangement of a foreign matter inspection apparatus according to the first embodiment of the present invention. FIG. 1 shows the apparatus when viewed from a z-direction toward an x-y plane, and FIGS. 2 and 3 show the apparatus when viewed from an x-direction toward a y-z plane. FIGS. 1 to 3 show the arrangement of the apparatus, and FIG. 4 shows the locus of incident light in the x-y plane.

An optical scan device for forming an arcuated optical scan line by scanning illumination light (incident light I) on the surface of a substrate (e.g., a mask used in the manufacture of a liquid crystal display) 35 will be described below with reference to FIG. 3.

Incident light I emitted by a laser 36 as a light source is expanded by an expander EX, is focused by a lens L, and is then incident on a mirror 42. Light rays 38, which are reflected by the mirror 42 fixed in the apparatus in a direction along an optical axis AX perpendicular to the substrate 35, are incident on a rotary mirror 39. The rotary mirror 39 is attached to a rotation shaft 40 having the optical axis AX as an axis, and is positioned so that its reflection surface is obliquely set with respect to the surface of the substrate 35. The mirror 39 is rotated by a motor 41.

The incident light I reflected by the rotary mirror 39 toward the surface of the substrate 35 reaches an incident point 50 on a surface M, to be inspected, of the substrate 35. The incident light I focused by the lens L, as described above, forms a spot on the surface of the substrate 35.

The position 50 where the incident light I reaches the surface M, to be inspected, of the substrate 35 depends on the direction (i.e., the rotation angle) of the mirror 39 with respect to the optical axis AX. More specifically, when a main control system 100 controls the motor 41 to rotate the rotary mirror 39 at an equal angular velocity to have the rotation shaft 40 as the center, the laser spot (incident light I) moves at an equal speed on the substrate 35 while forming an arcuated optical scan line C, as shown in FIG. 1. The rotation position of the motor 41 (the rotation angle of the mirror 39) is monitored by, e.g., a rotary encoder (not shown), and the rotation position information of the motor 41, i.e., the rotation angle information of the mirror 39, is input to the main control system 100.

In this manner, the light source 36, the expander EX, the lens L, the mirror 42, and the rotary mirror 39 constitute an optical scan device for forming an arcuated optical scan line by scanning the incident light I on the surface of the substrate 35.

Referring to FIG. 1, the optical scan direction agrees with the clockwise (CW) direction in FIG. 1, and a point 51 indicates the inspection start point. The illumination spot then reaches a point 52 as an inspection end point via a point 50. The optical scan line after the point 52 is not used in inspection, but the rotary scan continues, as indicated by a broken arrow A, and returns to the point 51 again.

On the other hand, as shown in FIGS. 1 and 4, a motor 47 and a feed screw 48 are arranged on a stage ST on which the substrate 35 is placed. Upon rotation of the motor 47, the stage ST and the substrate 35 can be reciprocally moved in the y-direction. In this manner, the motor 47 and the feed screw 48 constitute a moving device for moving the substrate 35 relative to the optical scan device.

As described above, by the rotary scan of the optical scan device and the equal-speed movement (indicated by an arrow 46 in FIG. 4), in the -y-direction, of the moving device, illumination light can be irradiated over a region 45 on the surface M, to be inspected, of the substrate 35 to have a sufficiently small luminance nonuniformity. More specifically, in FIG. 4, by the equal-speed translation of the substrate 35 in the direction of the arrow 46, the optical axis AX relatively moves to a position AX', and illumination light is irradiated in the region 45 with a sufficiently small luminance nonuniformity.

A light-receiving device for receiving scattered light from foreign matter attached onto the surface of the substrate 35 will be described below with reference to FIGS. 1 and 2.

Referring to FIG. 1, light-receiving elements 1 to 17 comprise, e.g., photomultipliers, and are juxtaposed at equal angular intervals to look into an optical scan line C from the obliquely upper positions, thus forming a right circular cone as a whole. More specifically, assuming a right circular cone which passes the centers of the light-receiving elements 1 to 17 and the bottom surface of which is located on the surface M to be inspected in FIG. 1, a portion of the contour of the bottom surface of this right circular cone matches the optical scan line C. On the other hand, an angle formed between the generator of the right circular cone and the surface of the substrate 35 is constant, and is, e.g., 55° in the case of FIG. 1.

The surfaces, facing the substrate 35, of the light-receiving elements 1 to 17, i.e., light-receiving surfaces 18 to 34, are set in an arcuated pattern to face the optical scan line C, so as to receive scattered light from a portion of the optical scan line C. The observation field (photometry region) of each light-receiving element overlaps those of the two neighboring light-receiving elements, and scattered light from any point on the optical scan line C can be received by a set of three continuous light-receiving elements.

More specifically, the light-receiving surface 22 of the light-receiving element 5 in FIG. 1 can receive light from a region C22 on the scan line C. Similarly, the light-receiving surface 23 of the light-receiving element 6 can receive light from a region C23, and the light-receiving surface 21 of the light-receiving element 4 can receive light from a region C21. Therefore, scattered light from a point P on the optical scan line C is detected by the light-receiving surfaces 21, 22, and 23.

Electrical signals 44 which are photoelectrically converted by the light-receiving elements 1 to 17 and represent the amounts of scattered light components received by the respective light-receiving elements are input to a signal processing device 37. The signal processing device 37 selects three neighboring light-receiving elements which can receive light from the inspection position (the position of illumination light) in accordance with the rotation angle information of the rotary mirror 39 from the main control system 100, and performs signal processing for the electrical signals from the selected light-receiving elements. More specifically, the signal processing device 37 selects the light-receiving element corresponding to the position of the incident light I on the optical scan line C and those on the two sides of the light-receiving element in accordance with the rotation angle information of the rotary mirror 39. In order to distinguish scattered light from a pattern edge with offset scattering directivity from scattered light from foreign matter with no scattering directivity, the signal processing device 37 removes scattering light from the pattern edge as noise by the directivity discrimination technique that has already been described in the paragraphs of the summary of the invention.

More specifically, the sizes (and layout) of the light-receiving surfaces are determined, so that the interval (i.e., the interval between spatial frequency regions of the two light-receiving surfaces on the U-V plane associated with an arc direction on the U-V plane corresponding to the arc defined by the light-receiving elements), in the direction of the scan line C (circumferential direction), of the light-receiving surfaces of the light-receiving elements located at the two ends of the three neighboring light-receiving elements of the light-receiving elements 1 to 17 becomes almost equal to the spatial frequency region of the incident light I (strictly speaking, the spatial frequency region of scattered light distributed in a space where the light-receiving elements are disposed).

Figure 5:
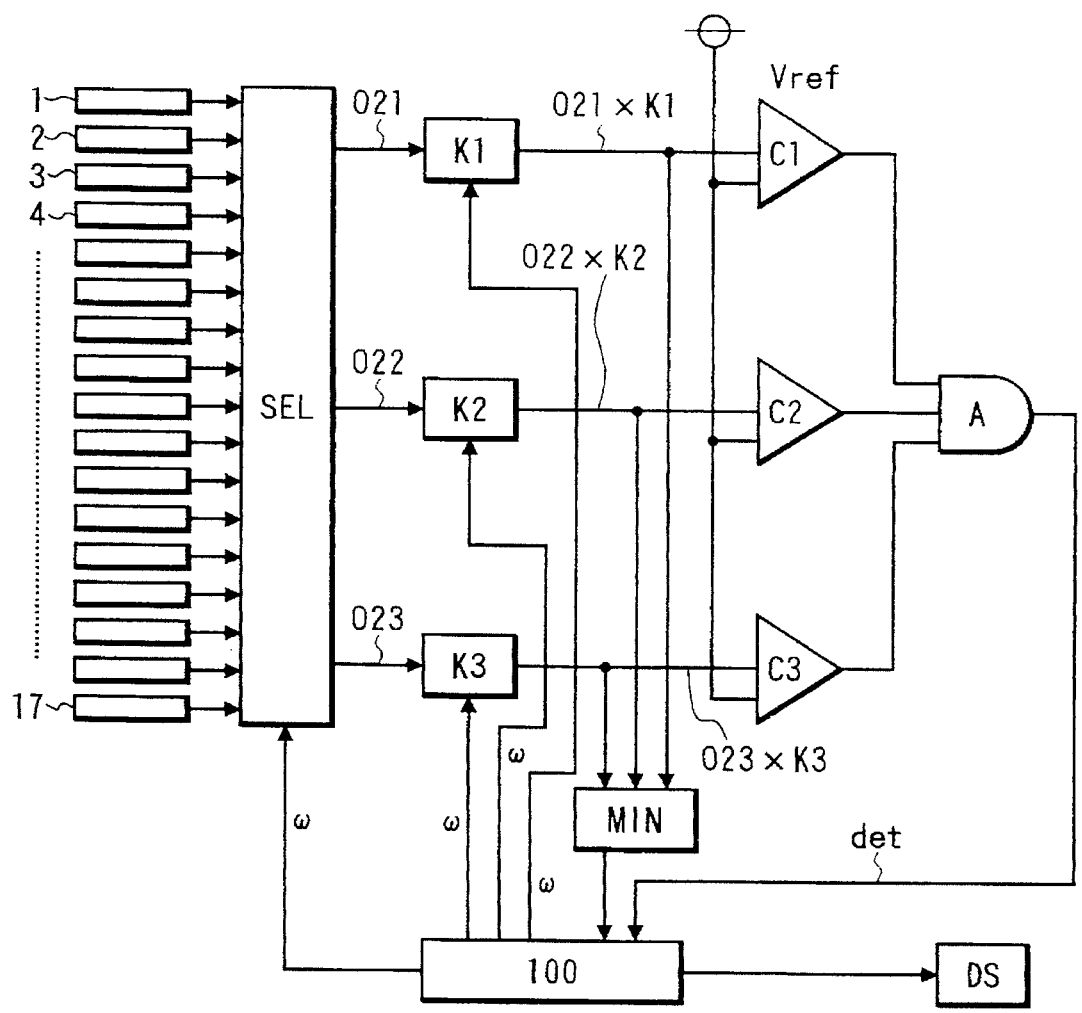
FIG. 5 is a block diagram showing the internal arrangement of a signal processing device shown in FIG. 1.
Figure 6A:
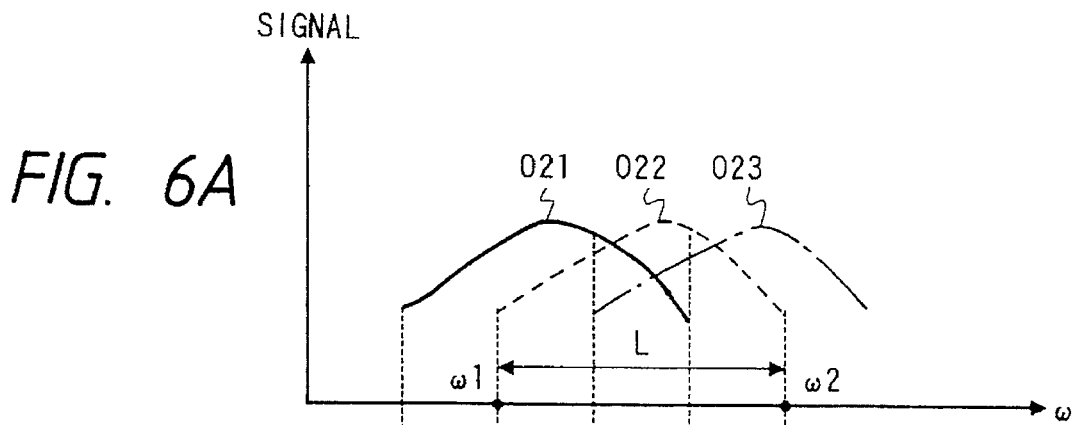
FIGS. 6A to 6C are graphs for explaining gain correction in the signal processing device shown in FIG. 5.
Figure 6B:
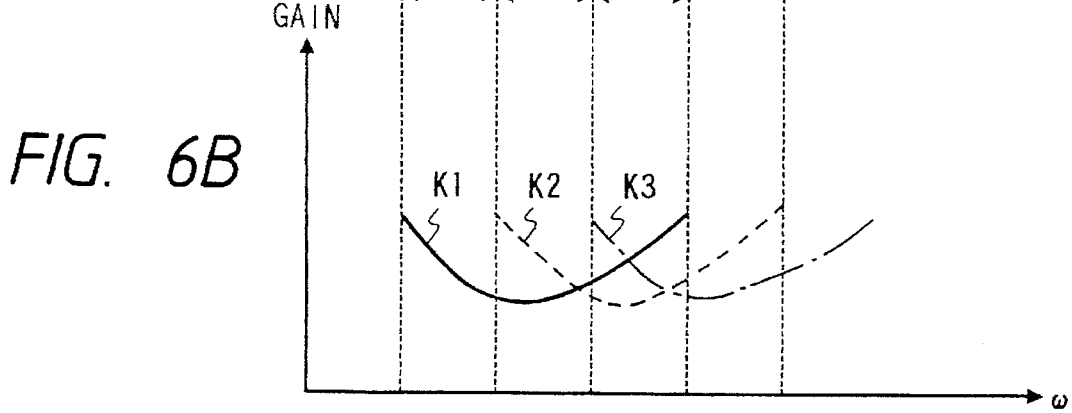
Figure 6C:
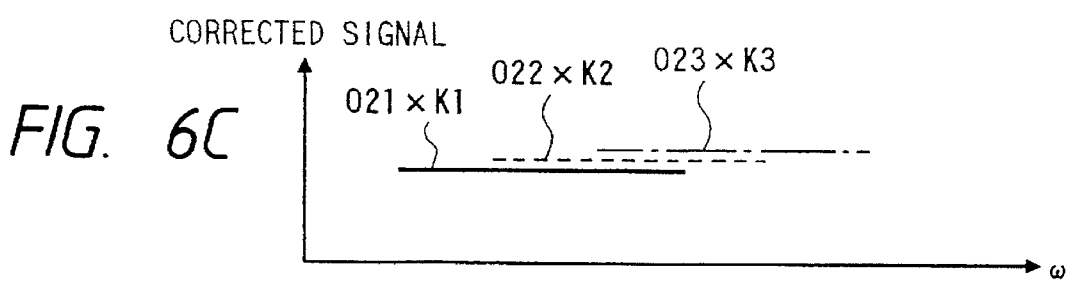

FIG. 5 is a block diagram showing the internal arrangement of the signal processing device shown in FIG. 1. FIGS. 6A to 6C are graphs for explaining gain correction in the signal processing device shown in FIG. 5.

The signal processing device shown in FIGS. 1 and 5 comprises a signal switching device SEL for receiving the electrical signals from the light-receiving elements 1 to 17. The signal switching device SEL selects three light-receiving elements, which can receive scattered light from the inspection point corresponding to the rotation angle, ω, of the rotary mirror 39, from the 17 light-receiving elements on the basis of the rotation angle ω of the rotary mirror 39 input from the main control system 100, and outputs the electrical signals from the three selected light-receiving elements.

As described above, of the light-receiving elements 1 to 17, only three neighboring light-receiving elements can simultaneously receive scattered light from a certain one point (inspection point) on the optical scan line C. Therefore, the three neighboring light-receiving elements which can simultaneously receive light from the inspection point are appropriately selected from the 17 light-receiving elements in accordance with the position of the inspection point, which depends on the rotation angle ω of the rotary mirror 39.

For example, in FIG. 1, light from the point P can be received by the light-receiving elements 4 to 6. Therefore, when the rotation angle ω of the rotary mirror 39 has reached a specific angle and illumination light has reached the point P, the light-receiving elements to be selected are the elements 4 to 6.

In FIG. 5, the light-receiving elements 4, 5, and 6 corresponding to the light-receiving surfaces 21, 22, and 23 are selected by the signal switching device SEL, and electrical signals O21, O22, and O23 from the light-receiving elements 4, 5, and 6 are output. The output signals O21, O22, and O23 are respectively input to variable-gain amplifiers K1, K2, and K3.

The variable-gain amplifiers K1, K2, and K3 perform gain correction on the basis of the rotation angle ω of the rotary mirror 39 input from the main control system 100. The gain correction operation will be described below with reference to FIGS. 6A to 6C.

FIG. 6A shows changes in output electrical signals O21, O22, and O23 with respect to the angle ω of the rotary mirror, while the magnitude of the signal is plotted along the ordinate, and the rotation angle ω is plotted along the abscissa. Assume that a uniform scattering member for sensitivity calibration, which can generate the same amount of scattered light independently of the illumination position of light on the optical scan line, is set on the substrate surface.

In FIG. 6A, the electrical signal O22 corresponds to the light-receiving surface 22 of the light-receiving element 5, and an illumination region in the rotation angle range from ω1 to ω2 corresponds to the region C22 in FIG. 1. Therefore, the electrical signal O22 is detected in the rotation angle range from ω1 to ω2. Although the amount of scattered light is constant, the distribution of the electrical signal O22 is expressed by an upward convex curve in FIG. 6A due to a change in numerical aperture (NA) on the object side of the light-receiving surface 22.

Let L be the width of the angle range from ω1 to ω2. Then, the electrical signals O21 and O23 are respectively output as upward convex curves in FIG. 6A on the left and right sides in FIG. 6A of the electrical signal O22 each to have a phase difference of L/3.

In this manner, the output electrical signals O21, O22, and O23 vary depending on the rotation angle ω of the rotary mirror 39, i.e., the scan position of the illumination light. Therefore, the electrical signals O21, O22, and O23 are gain-corrected by the variable-gain amplifiers K1, K2, and K3 having correction curves k1, k2, and k3 shown in FIG. 6B. As a result, as shown in FIG. 6C, the corrected electrical signals k1×O21, k2×O22, and k3×O23 become almost constant independently of the rotation angle ω. Note that the phase of the abscissa is locked in FIGS. 6A to 6C.

The corrected signals k1×O21, k2×O22, and k3×O23 are respectively supplied from the variable-gain amplifiers K1, K2, and K3 to a minimum value selector MIN. The minimum value selector MIN obtains a minimum value $S_{min}$ from the input three corrected signal values, and outputs the obtained value to the main control system 100. The main control system 100 specifies the size of foreign matter on the basis of the minimum value $S_{min}$. The reason why the minimum value is used for specifying the size of foreign matter is to remove noise from an edge when a pattern edge and foreign matter are present together.

Also, the corrected signals k1×O21, k2×O22, and k3×O23 are respectively parallelly input to three comparators C1, C2, and C3. Each comparator binarizes the input signal by comparing it with a threshold value $V_{ref}$ which has a sufficiently high level in view of the levels of electrical noise and optical noise. The binarized three signals are input to an AND gate A, and when all the input signals to the three comparators exceed the threshold value $V_{ref}$, the AND gate A outputs a foreign matter detection signal Det to the main control system 100. The main control system 100 fetches the minimum value from the minimum value selector MIN in response to the foreign matter detection signal Det as a trigger. As described above, the main control system 100 determines the size of foreign matter on the basis of the minimum value, and outputs the size, shape, and the like of foreign matter to a display unit DS together with the position of foreign matter on the surface to be inspected.

Figure 7:
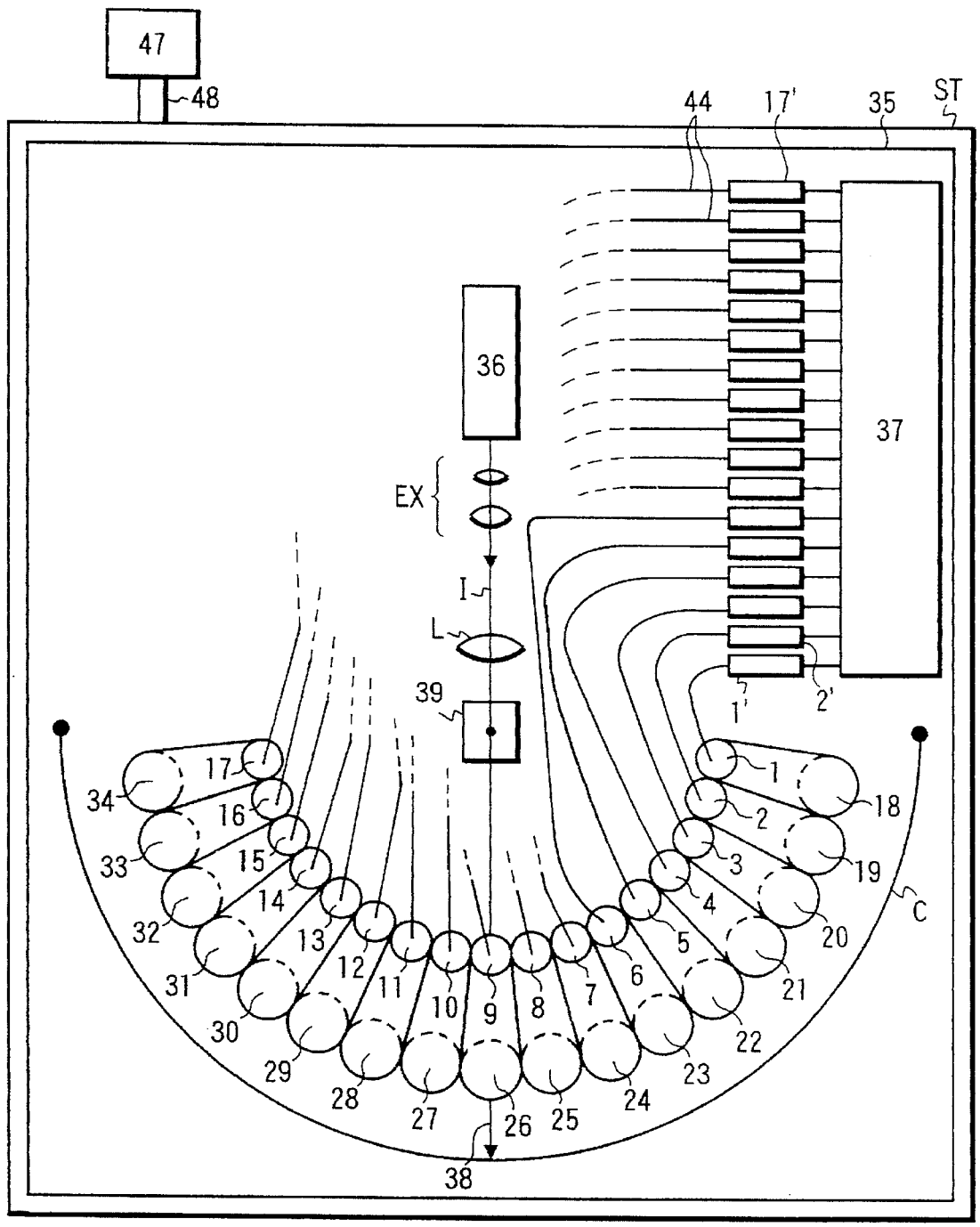
FIG. 7 is a schematic x-y plan view showing the arrangement of a foreign matter inspection apparatus according to the second embodiment of the present invention.

FIG. 7 is a schematic view showing the arrangement of a foreign matter inspection apparatus according to the second embodiment of the present invention. The apparatus of this embodiment has substantially the same arrangement as that of the apparatus of the first embodiment, except for the following basic difference. That is, in the first embodiment, the light-receiving elements comprise photomultipliers and perform photoelectric conversion, while in this embodiment, light-receiving elements 1 to 17 comprise simple optical fibers, and photoelectric conversion is performed by photoelectric conversion elements 1' to 17' connected to the light-receiving elements 1 to 17. This embodiment will be described below while paying attention to the difference in arrangement from the first embodiment, and a repetitive description in the overall operation will be avoided.

More specifically, in this embodiment, the light-receiving surfaces 18 to 34 are merely the incident end faces of the optical fibers, and the output end faces of the optical fibers 1 to 17 are respectively connected to the photoelectric conversion elements 1' to 17'. Therefore, the amounts of light received by the light-receiving surfaces 18 to 34 are converted into electrical signals by the photoelectric conversion elements 1' to 17', and the converted signals are input to the signal processing device 37.

Note that the operation in the signal processing device 37 is the same as that in the first embodiment, and a detailed description thereof will be omitted.

Figure 8:
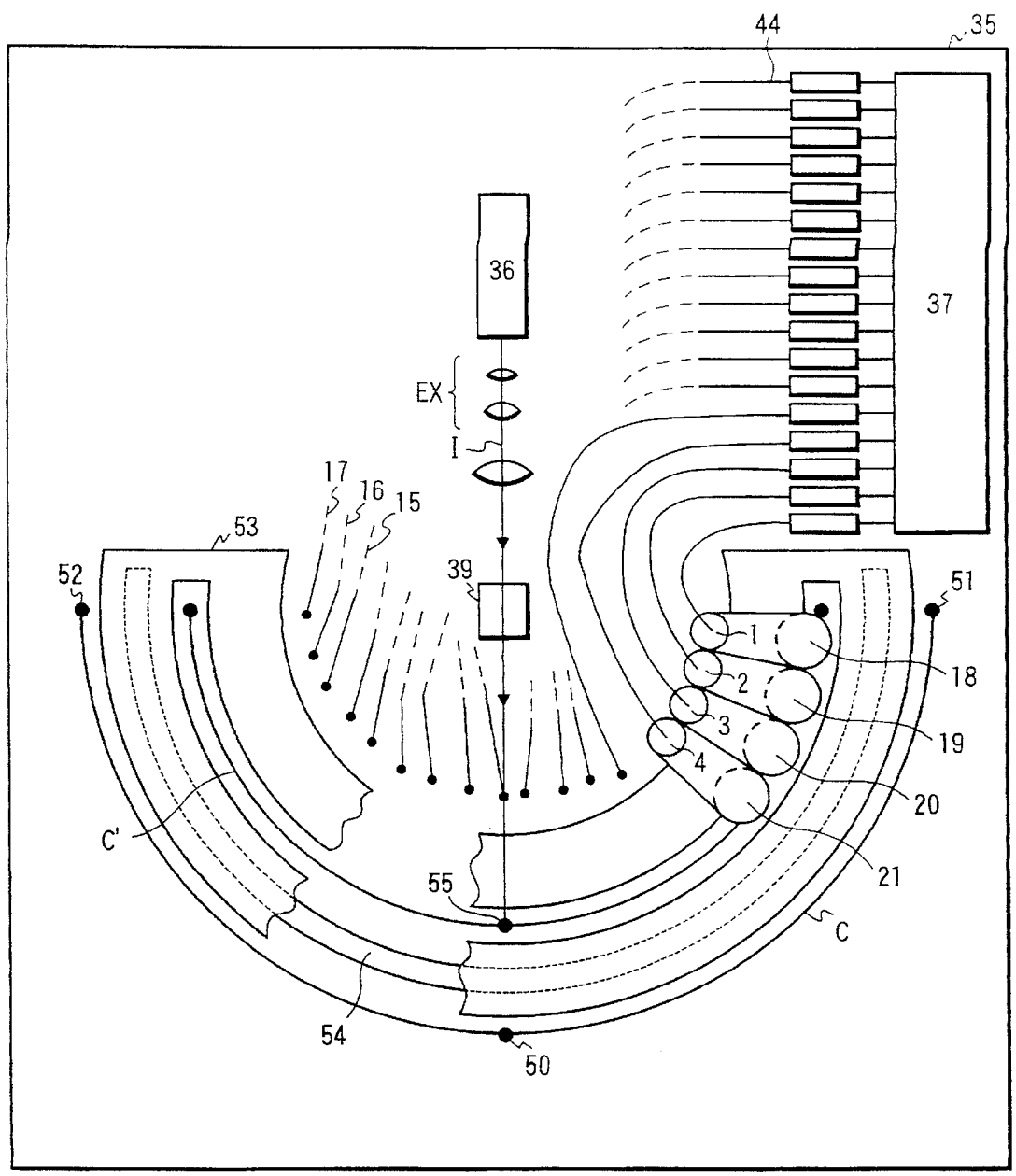
FIG. 8 is a schematic x-y plan view showing the arrangement of a foreign matter inspection apparatus according to the third embodiment of the present invention.
Figure 9:
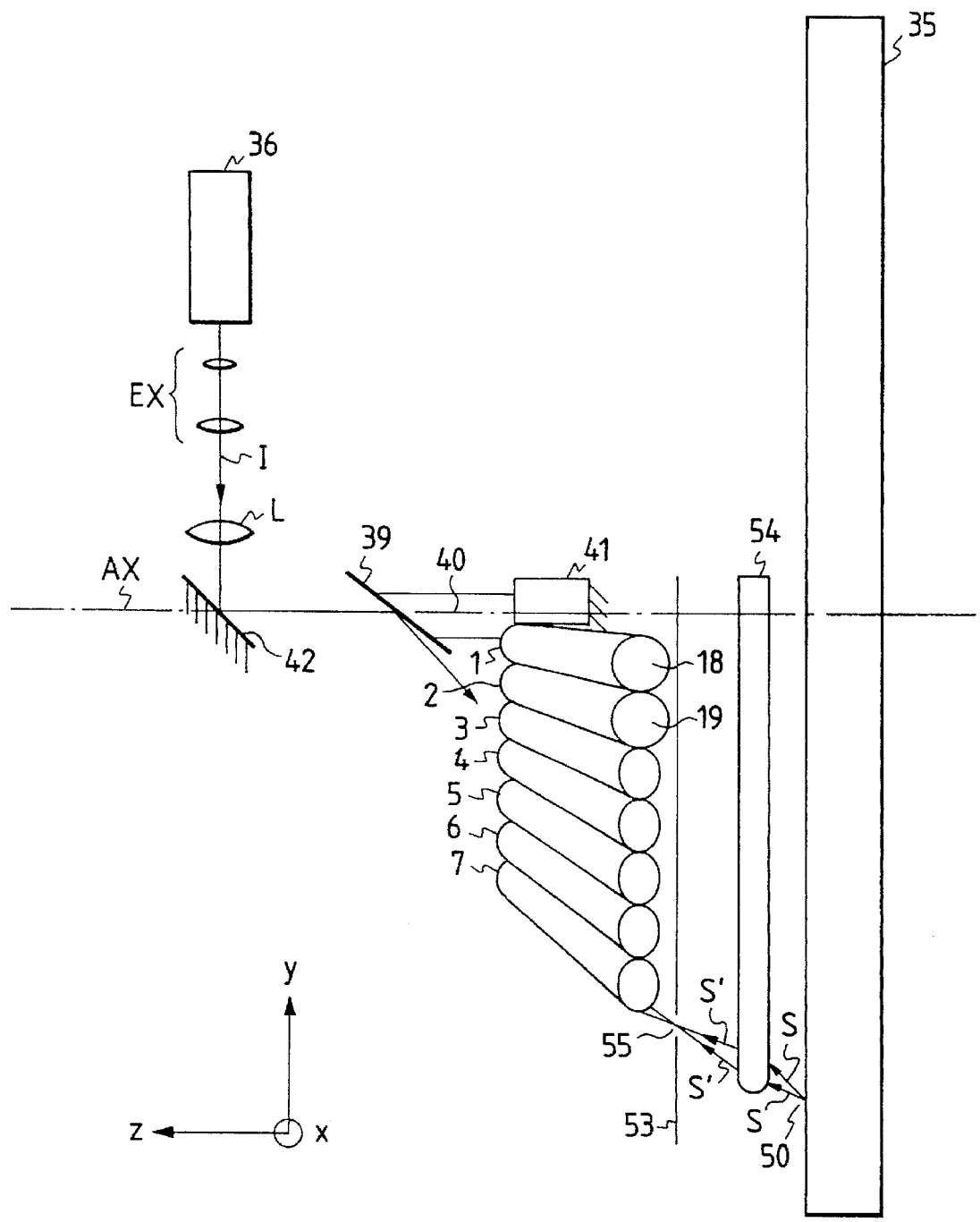
FIG. 9 is a schematic y-z plan view showing the arrangement of the foreign matter inspection apparatus according to the third embodiment of the present invention.

FIGS. 8 and 9 are schematic views showing the arrangement of a foreign matter inspection apparatus according to the third embodiment of the present invention. Note that FIG. 8 is an x-y plan view, and FIG. 9 is a y-z plan view.

The apparatus of this embodiment has substantially the same arrangement as that of the apparatus of the second embodiment, except for the following basic difference. That is, in the second embodiment, the light-receiving surfaces 18 to 34 of the light-receiving elements 1 to 17 directly face the optical scan line C on the substrate 35, while in this embodiment, the light-receiving surfaces 18 to 34 (the light-receiving surfaces 22 to 34 are not shown) of the light-receiving elements 1 to 17 face an optical scan line image C' formed by a doughnut-shaped lens 54. Note that an arcuated slit 53 is inserted between the light-receiving surfaces 18 to 34 of the light-receiving elements 1 to 17, and the doughnut-shaped lens 54. This embodiment will be described below while paying attention to the difference in arrangement from the second embodiment, and a repetitive description in the overall operation will be avoided.

As shown in FIG. 9, scattered light S generated from an illuminated inspection point 50 on the substrate 35 is refracted by the arcuated (doughnut-shaped) lens 54, and forms a spot image at a point 55. The arcuated lens 54 comprises, e.g., an optical fiber, and has refracting power in only the radial direction but has no refracting power in the circumferential direction. In this manner, the image 55 of the inspection point 50 is formed on a light-transmitting portion of the arcuated slit 53 by the arcuated lens 54, and becomes incident on the light-receiving surfaces as a light beam S'. Therefore, of the spatial frequency components of the scattered light generated from the inspection point, components in the circumferential direction (the layout direction of the light-receiving elements) are preserved and reach the light-receiving elements. More specifically, it can be considered that, in the circumferential direction of the arcuated lens 54, the light-receiving surfaces of the light-receiving elements are disposed on the Fourier transformation plane (U-V plane) with respect to the pattern on the substrate.

As shown in FIG. 8, the inspection point 50 forms the arcuated optical scan line C by the rotary scan operation, and its spot image 55 constitutes the arcuated optical scan line image C'. Note that the arcuated slit 53 can shield unnecessary stray light generated from a portion other than the optical scan line image C'.

Figure 10:
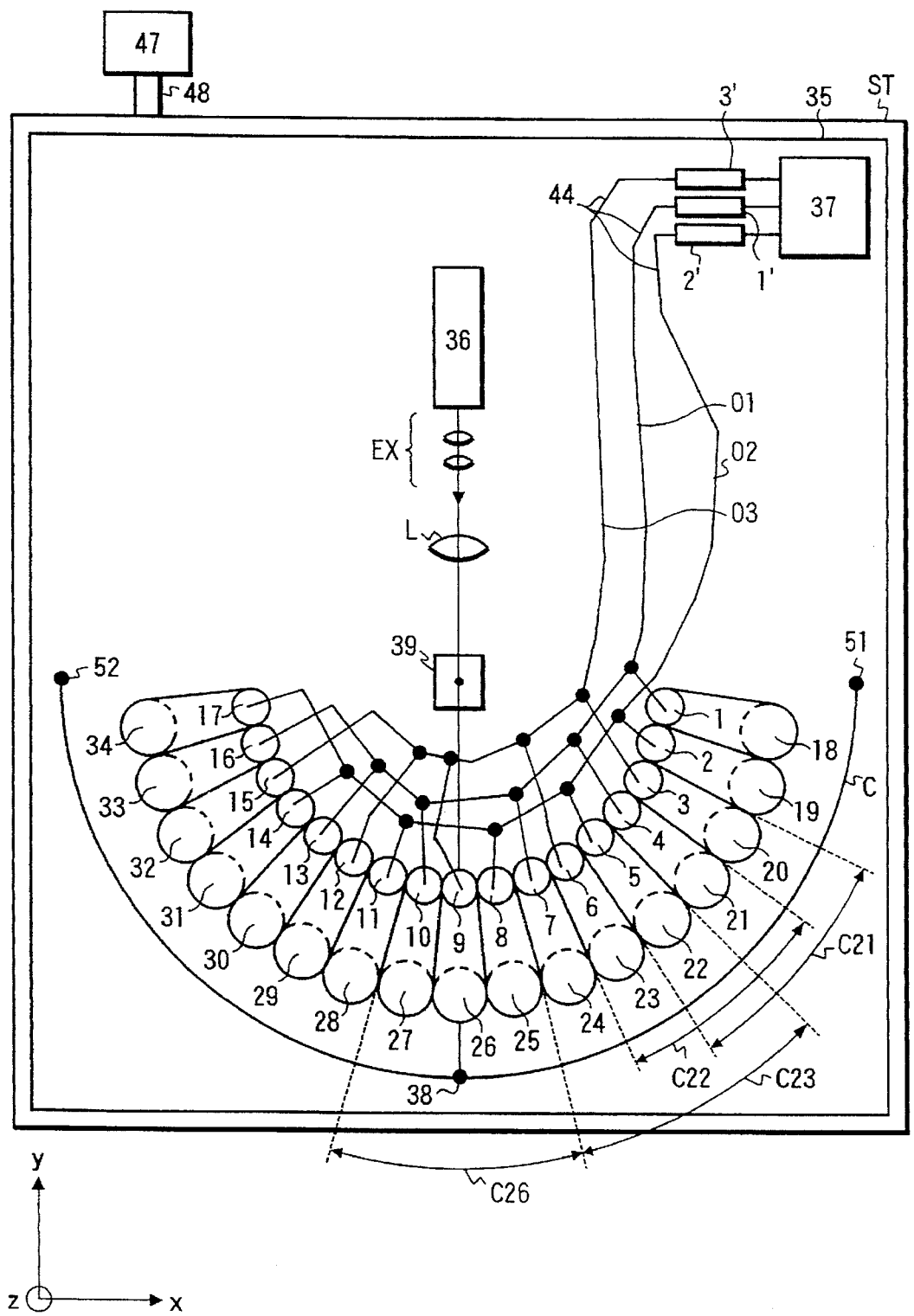
FIG. 10 is a schematic x-y plan view showing the arrangement of a foreign matter inspection apparatus according to the fourth embodiment of the present invention.

FIG. 10 is a schematic view showing the arrangement of a foreign matter inspection apparatus according to the fourth embodiment of the present invention. The apparatus of this embodiment has substantially the same arrangement as that of the apparatus of the second embodiment, except for the following basic difference. In the second embodiment, the light-receiving elements 1 to 17 are selected in the signal processing device 37, while in this embodiment, the light-receiving elements 1 to 17 are selected in a stage before the signal processing device 37. This embodiment will be described below while paying attention to the difference in arrangement from the second embodiment, and a repetitive description in the overall operation will be avoided.

Referring to FIG. 10, the light-receiving elements 1 to 17 comprise optical fibers, each of which is a small branch divided from a large trunk. More specifically, every fourth ones of the light-receiving elements are connected to optical fibers O1 to O3 as large trunks. For example, the light-receiving elements 1, 4, 7, 10, and 13 are connected to the optical fiber O1, the light-receiving elements 3, 6, 9, 12, and 15 are connected to the optical fiber O2, and the light-receiving elements 2, 5, 8, 11, 14, and 17 are connected to the optical fiber O3. Furthermore, the optical fibers O1, O2, and O3 are respectively connected to photoelectric conversion elements 1', 2', and 3'.

In this embodiment and the above-mentioned embodiments, each light-receiving element shares a photometry region with two neighboring light-receiving elements, but does not share a photometry region with light-receiving elements outside the two neighboring ones. Therefore, when the light-receiving elements 1 to 17 are connected to the optical fibers O1 to O3 in the system shown in FIG. 10, three arbitrary neighboring light-elements are connected to the optical fibers O1, O2, and O3.

Furthermore, the light-receiving elements 6 and 9 connected to the optical fiber O3 will be examined below. Although photometry regions C23 and C26 on the optical scan line C corresponding to the light-receiving surfaces 23 and 26 of the light-receiving elements 6 and 9 are successively present, light from one point on the photometry region C23 or C26 is received by the light-receiving surface 23 or 26, and is not simultaneously received by both the light-receiving elements 23 and 26. More specifically, no crosstalk is generated.

In this manner, selection of the light-receiving elements 1 to 17 is attained by the signal switching device SEL in FIG. 5 in the first embodiment, but is attained by connections between the light-receiving elements 1 to 17 and the optical fibers O1 to O3 in this embodiment. Therefore, in this embodiment, the signal switching device SEL need not be arranged in the signal processing device 37.

More specifically, with the connection arrangement of this embodiment, a minimum of only three photoelectric conversion elements are required, and the arrangement of the signal processing device 37 connected to the photoelectric conversion elements 1' to 3' can be simplified.

Figure 11:
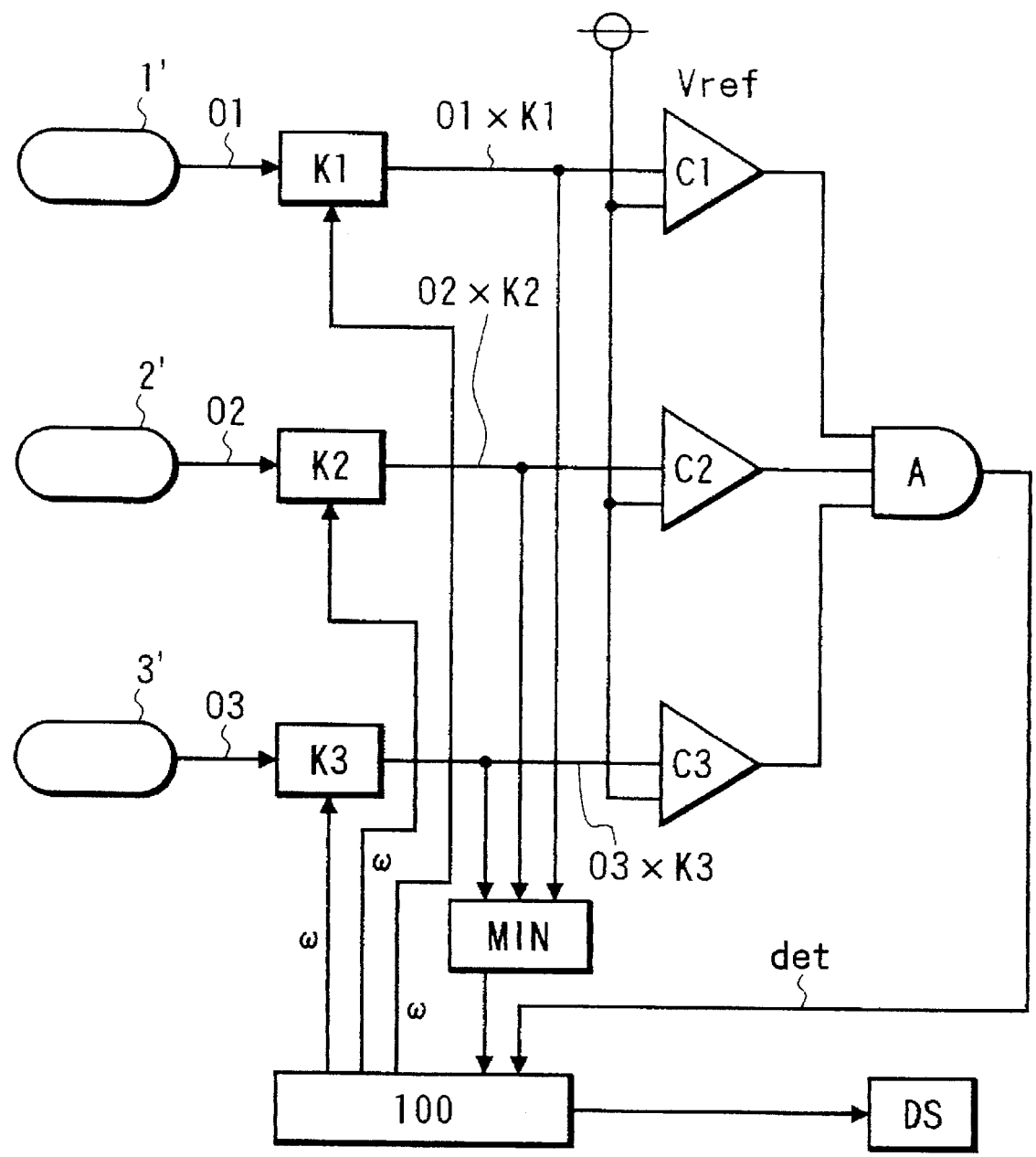
FIG. 11 is a block diagram showing the internal arrangement of a signal processing device of the fourth embodiment shown in FIG. 10.
Figure 13A:
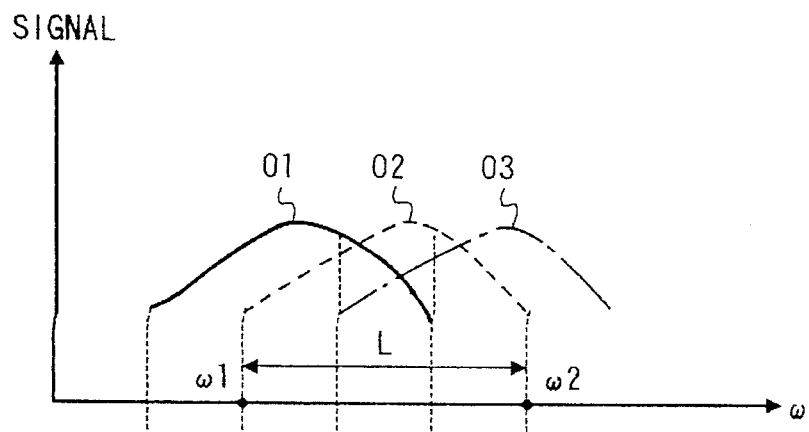
FIGS. 13A to 13C are graphs for explaining gain correction in the signal processing device shown in FIG. 11.
Figure 13B:
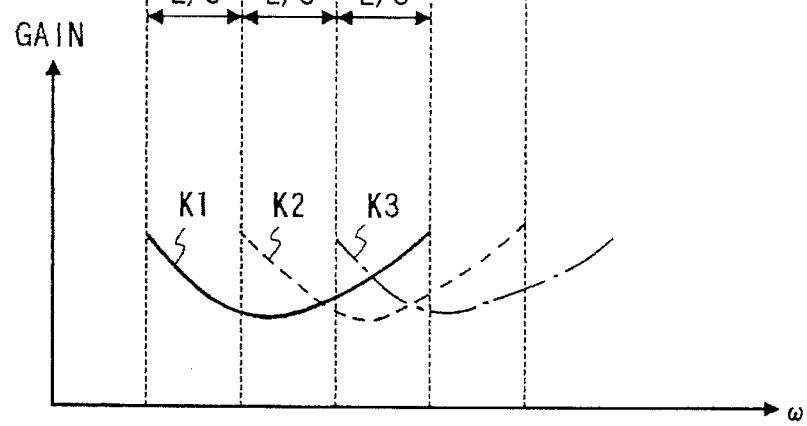
Figure 13C:
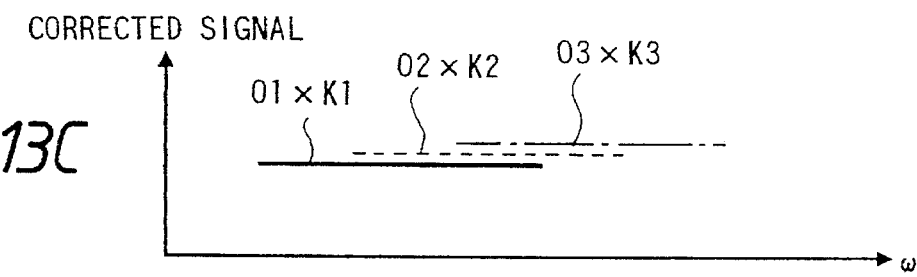
Figure 14:
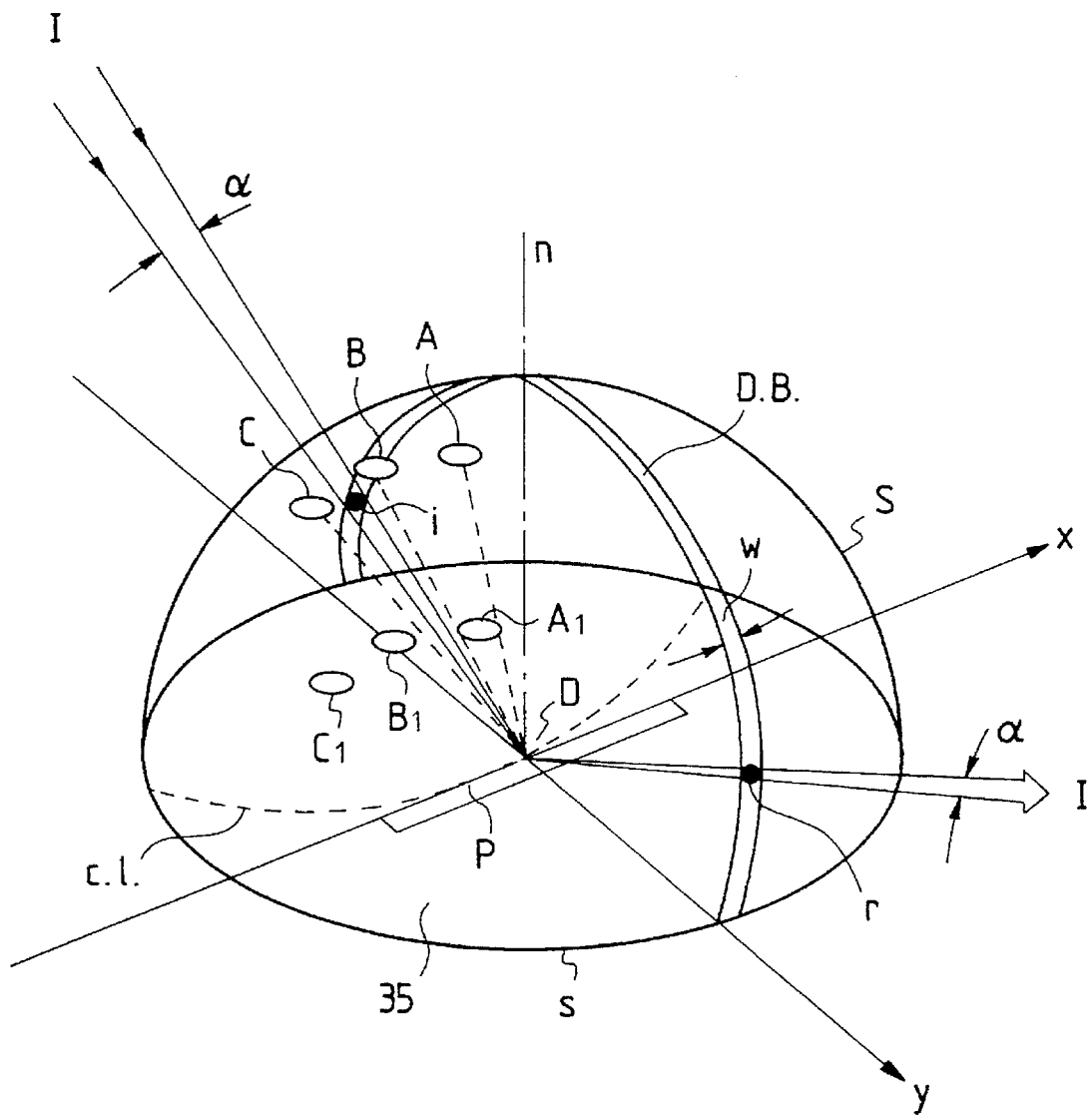
FIG. 14 is a view for explaining a technique for optically removing pattern edge noise, and showing the distribution of respective light beams on the spherical surface of a virtual sphere S.
Figure 15A:
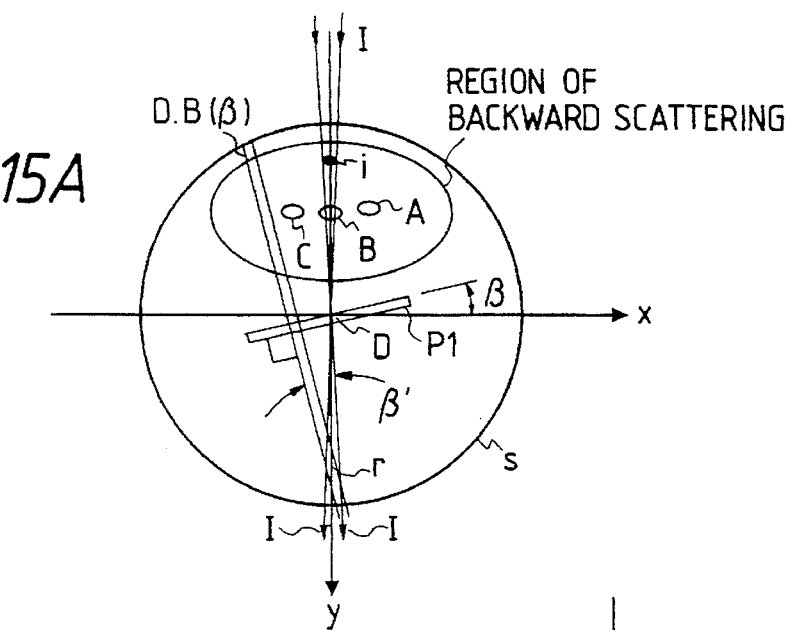
Figure 15B:
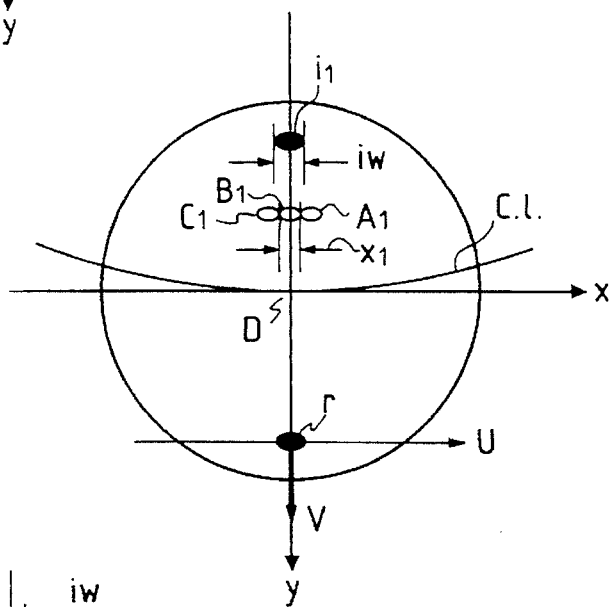
Figure 15C:
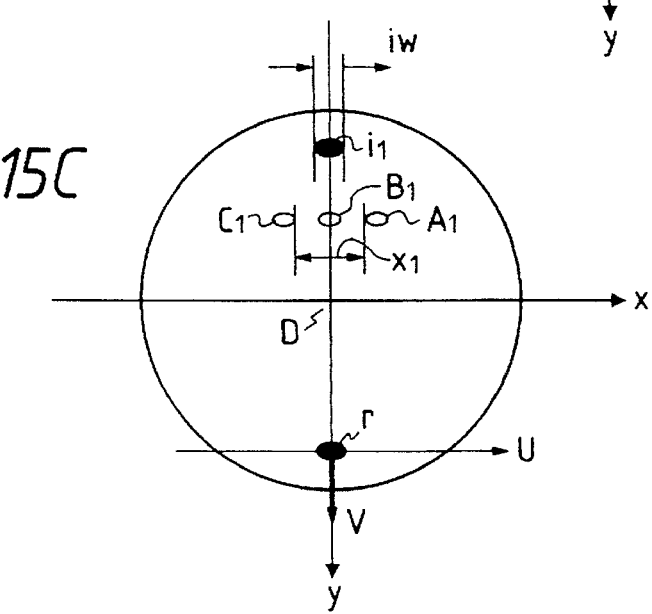

FIG. 11 is a block diagram showing the internal arrangement of the signal processing device shown in FIG. 10 of this embodiment. FIGS. 13A to 13C are graphs for explaining gain correction in the signal processing device in FIG. 11.

The signal processing device of this embodiment shown in FIG. 11 has substantially the same arrangement of the signal processing device of the first embodiment shown in FIG. 5, except for the following basic difference. That is, in this embodiment, the signal switching device SEL is omitted, and electric signals O1, O2, and O3 are directly input from the photoelectric conversion elements 1', 2', and 3' to the variable-gain amplifiers K1, K2, and K3.

Note that the variable-gain amplifiers K1, K2, and K3 perform gain correction on the basis of the rotation angle ω of the rotary mirror 39 input from the main control system 100, as shown in FIGS. 13A to 13C, as in the first embodiment, and a repetitive description thereof will be omitted.

Figure 12:
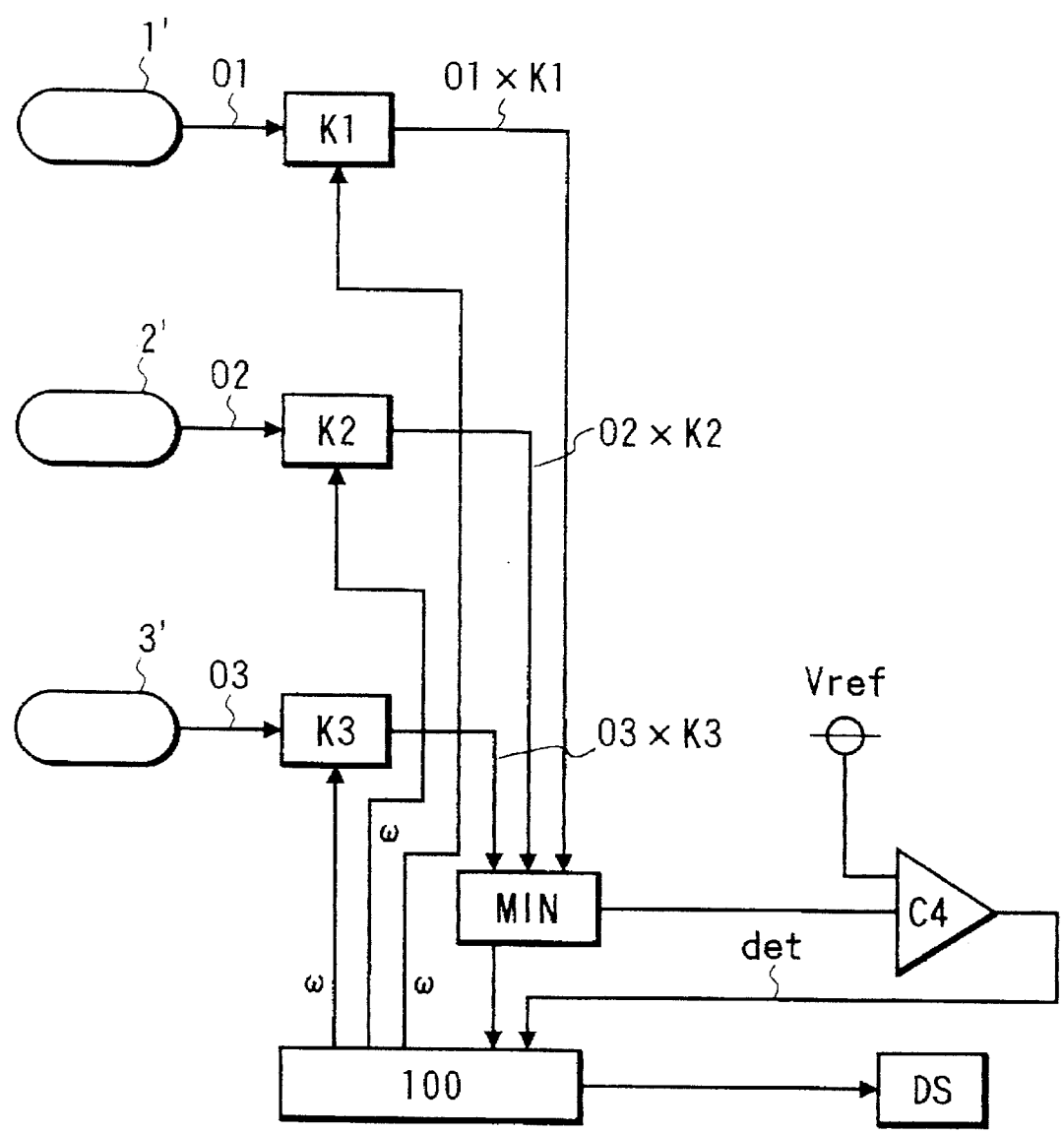
FIG. 12 is a block diagram showing a modification of the signal processing device which can be applied to the fourth embodiment.

FIG. 12 is a block diagram showing a modification of the signal processing device which can be applied to this embodiment. In the apparatus shown in FIG. 12, a comparator C4 binarizes a minimum value from the minimum value selector MIN by comparing the minimum value with the threshold value $V_{ref}$ having a sufficiently high level in terms of the levels of electrical noise and optical noise. More specifically, the comparator C4 outputs a foreign matter detection signal Det to the main control system 100 when the minimum value from the minimum value selector MIN exceeds the threshold value $V_{ref}$. The main control system 100 fetches the minimum value from the minimum value selector MIN in response to this foreign matter detection signal Det as a trigger. The main control system 100 then determines the size of foreign matter on the basis of the minimum value, and outputs the size, shape, and the like of foreign matter to a display unit DS together with the position of foreign matter on the surface to be inspected.

In the description of the above embodiments and functions, there are three light-receiving elements which can observe one point on the substrate. However, the number of light-receiving elements that can receive scattered light from one point is not particularly limited as long as it is two or more.

Therefore, it is intended that the invention not be limited to the preferred embodiments described herein, but that the invention will include all embodiments falling within the scope of the appended claims.

What is claimed is:

1. A foreign matter inspection apparatus for optically inspecting foreign matter attached to a surface of a substrate on which a pattern is formed, comprising:

an optical scan device for forming an arcuated optical scan line by scanning illumination light on the surface of the substrate;

a moving device for moving the substrate relative to the optical scan line in a predetermined direction;

a light-receiving device for receiving scattered light from the foreign matter attached to the surface of the substrate, and outputting an electrical signal corresponding to an intensity of the scattered light; and a signal processing device for detecting the foreign matter based on the electrical signal from said light-receiving device, wherein said light-receiving device comprises a plurality of light-receiving elements which are arranged in an arcuated pattern at positions where said light-receiving elements look into the arcuated optical scan line, and independently output electrical signals corresponding to light intensities of the scattered light, and each of said plurality of light-receiving elements comprises an optical fiber, an incident end face of which faces the surface of the substrate.

2. An apparatus according to claim 1, further comprising:

a selection device for selecting at least two neighboring light-receiving elements from said plurality of light-receiving elements in accordance with a position of the illumination light on the surface of the substrate, and wherein said signal processing device comprises a comparison device for comparing values of the electrical signals from the at least two selected light-receiving elements with a predetermined threshold value, and detects the foreign matter based on the number of electrical signals that exceed the predetermined threshold value.

3. An apparatus according to claim 2, wherein said signal processing device comprises a gain correction device for correcting gains of the electrical signals from the at least two selected light-receiving elements in correspondence with the position of the illumination light on the surface of the substrate.

4. An apparatus according to claim 3, wherein said gain correction device comprises a variable-gain amplifier.

5. A foreign matter inspection apparatus for optically inspecting foreign matter attached to a surface of a substrate on which a pattern is formed, comprising:

an optical scan device for forming an arcuated optical scan line by scanning illumination light on the surface of the substrate;

a moving device for moving the substrate relative to the optical scan line in a predetermined direction;

a light-receiving device for receiving scattered light from the foreign matter attached to the surface of the substrate, and outputting an electrical signal corresponding to an intensity of the scattered light; and a signal processing device for detecting the foreign matter based on the electrical signal from said light-receiving device, wherein said optical scan device comprises:
      a reflection device having a reflection surface which is obliquely set with respect to the surface of the substrate;
      a driving device for rotating said reflection device about an axis perpendicular to the surface of the substrate;
      a focusing optical system for focusing the illumination light reflected by said reflection device onto the surface of the substrate in a spot pattern; and
      a control device for controlling said driving device to move the light focused in the spot pattern along the arcuated optical scan line upon rotation of said reflection device, wherein said light-receiving device comprises a plurality of light-receiving elements which are arranged in an arcuated pattern at positions where said light-receiving elements look into the arcuated optical scan line, and independently output electrical signals corresponding to light intensities of the scattered light, and each of said plurality of light-receiving elements comprises an optical fiber, an incident end face of which faces the surface of the substrate.

6. An apparatus according to claim 5, further comprising:

a selection device for selecting at least two neighboring light-receiving elements from said plurality of light-receiving elements in accordance with a position of the illumination light on the surface of the substrate, and wherein said signal processing device comprises a comparison device for comparing values of the electrical signals from the at least two selected light-receiving elements with a predetermined threshold value, and detects the foreign matter based on the number of electrical signals that exceed the predetermined threshold value.

7. An apparatus according to claim 6, wherein said signal processing device comprises a gain correction device for correcting gains of the electrical signals from the at least two selected light-receiving elements in correspondence with the position of the illumination light on the surface of the substrate.

8. An apparatus according to claim 7, wherein said gain correction device comprises a variable-gain amplifier.

9. A foreign matter inspection apparatus for optically inspecting foreign matter attached to a surface of a substrate on which a pattern is formed, comprising:

an optical scan device for forming an arcuated optical scan line by scanning illumination light on the surface of the substrate;

a moving device for moving the substrate relative to the optical scan line in a predetermined direction;

a light-receiving device for receiving scattered light from the foreign matter attached to the surface of the substrate, and outputting an electrical signal corresponding to an intensity of the scattered light; and a signal processing device for detecting the foreign matter based on the electrical signal from said light-receiving device, wherein said optical scan device comprises:
      a reflection device having a reflection surface which is obliquely set with respect to the surface of the substrate;
      a driving device for rotating said reflection device about an axis perpendicular to the surface of the substrate;
      a focusing optical system for focusing the illumination light reflected by said reflection device onto the surface of the substrate in a spot pattern; and
      a control device for controlling said driving device to move the light focused in the spot pattern along the arcuated optical scan line upon rotation of said reflection device, wherein said light-receiving device comprises a lens of arcuate shape which has a light-receiving surface for receiving the scattered light, and refracting power in a direction perpendicular to the optical scan line but has no refracting power in a direction parallel to the optical scan line, so as to form an image of the arcuated optical scan line from the light received by the light-receiving surface.

10. An apparatus according to claim 9, wherein said lens of arcuate shape comprises an optical fiber which is bent in an arcuated shape along the optical scan line.

11. An apparatus according to claim 9, wherein said light-receiving device comprises a field stop consisting of an arcuated slit for limiting the scattered light passing through said lens of arcuate shape, and said field stop is arranged at a position substantially optically conjugate with the surface of the substrate where the illumination light is focused in the spot pattern with respect to said lens of arcuate shape.

12. An apparatus according to claim 10, wherein said light-receiving device comprises a field stop consisting of an arcuated slit for limiting the scattered light passing through said lens of arcuate shape, and said field stop is arranged at a position substantially optically conjugate with the surface of the substrate where the illumination light is focused in the spot pattern with respect to said lens of arcuate shape.

\* \* \* \* \*